(12) United States Patent
Crowell et al.

(10) Patent No.: US 6,232,337 B1
(45) Date of Patent: May 15, 2001

(54) SELECTIVE $\beta_3$ ADRENERGIC AGONISTS

(75) Inventors: Thomas Alan Crowell; Charles David Jones, both of Indianapolis, IN (US); Anthony John Shuker, Atlanta, GA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/554,422

(22) PCT Filed: Dec. 2, 1998

(86) PCT No.: PCT/US98/25516

§ 371 Date: May 12, 2000

§ 102(e) Date: May 12, 2000

(87) PCT Pub. No.: WO99/29672

PCT Pub. Date: Jun. 17, 1999

Related U.S. Application Data

(60) Provisional application No. 60/067,837, filed on Dec. 5, 1997.

(51) Int. Cl.[7] ............................ A61K 31/415; A61P 3/10; C07D 231/18
(52) U.S. Cl. ........................................ 514/407; 548/370.1
(58) Field of Search ........................... 548/370.1; 514/407

(56) References Cited

U.S. PATENT DOCUMENTS 5,541,197   7/1996   Fisher et al. .

FOREIGN PATENT DOCUMENTS

WO 97/10822   3/1997   (WO) .
WO 97/10825   3/1997   (WO) .

Primary Examiner—Robert W. Ramsuer
(74) Attorney, Agent, or Firm—Gilbert T. Voy

(57) ABSTRACT

The present invention is in the field of medicine, particularly in the treatment of Type II diabetes and obesity. More specifically, the present invention relates to selective $\beta_3$ receptor agonists useful in the treatment of Type II diabetes and obesity. The invention provides compounds and methods of treating Type II diabetes and obesity, comprising administering to a mammal in need thereof compounds of formula (I) or a pharmaceutically acceptable salt thereof. The variables of formula (I) have the meanings defined herein.

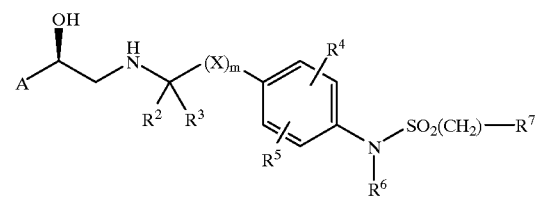

16 Claims, No Drawings

SELECTIVE β₃ ADRENERGIC AGONISTS

RELATED APPLICATIONS

This application claims the benefit of U.S. Provisional Application No. 60/067,837 filed on Dec. 5, 1997, the entire teachings of which are incorporated herein by reference.

FIELD OF INVENTION

The present invention is in the field of medicine, particularly in the treatment of Type II diabetes and obesity. More specifically, the present invention relates to selective $\beta_3$ adrenergic receptor agonists useful in the treatment of Type II diabetes and obesity.

BACKGROUND OF THE INVENTION

The current preferred treatment for Type II, non-insulin dependent, diabetes as well as obesity is diet and exercise, with a view toward weight reduction and improved insulin sensitivity. Patient compliance, however, is usually poor. There are no currently approved medications that adequately treat either Type II diabetes or obesity. The invention described herein is directed toward an effective and timely treatment for these serious diseases.

One recently recognized therapeutic opportunity involves the relationship between adrenergic receptor stimulation and anti-hyperglycemic effects. Compounds that act as $\beta_3$ adrenergic receptor agonists have been shown to exhibit a marked effect on lipolysis, thermogenesis, and serum glucose levels in animal models of Type II diabetes.

The $\beta_3$ receptor, which is found in several types of human tissue including human fat tissue, has roughly 50% homology to the $\beta_1$ and $\beta_2$ receptor subtypes yet is considerably less abundant. The importance of the $\beta_3$ receptor is a relatively recent discovery since the amino-acid sequence of the human receptor was only elucidated in the late 1980's. A large number of publications have appeared in recent years reporting success in discovery of agents that stimulate the $\beta_3$ receptor. Despite these recent developments there remains a need to develop a selective $\beta_3$ receptor agonist which has both high intrinsic activity and minimal agonist activity against the $\beta_1$ and $\beta_2$ receptors.

SUMMARY OF INVENTION

The present invention provides methods of treating Type II diabetes, treating obesity, and stimulating the $\beta_3$ receptor which comprise administering to a patient in need thereof a compound described by Formula I below.

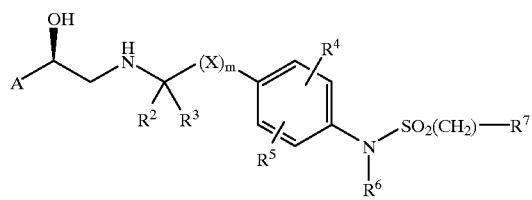

(I)

where n is 0 or 2;
m is 0 to 5;
r is 0 to 3;

A is

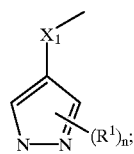

$X_1$ is
(1) —O—$CH_2$—,
(2) —S—$CH_2$—, or
(3) a bond;

$R^1$ is
(1) hydroxy,
(2) oxo,
(3) halogen,
(4) cyano,
(5) $NR^8R^8$,
(6) $SR^8$,
(7) trifluoromethyl,
(8) $C_1$–$C_{10}$ alkyl,
(9) $OR^8$,
(10) $SO_2R^9$,
(11) $OCOR^9$,
(12) $NR^8COR^9$,
(13) $COR^9$,
(14) $NR^8SO_2R^9$,
(15) $NR^8CO_2R^8$, or
(16) $C_1$–$C_{10}$ alkyl substituted by hydroxy, halogen, cyano, $NR^8R^8$, $SR^8$, trifluoromethyl, $OR^8$, $C_3$–$C_8$ cycloalkyl, phenyl, $NR^8COR^9$, $COR^9$, $SO_2R^9$, $OCOR^9$, $NR^8SO_2R^9$ or $NR^8CO_2R^8$;

$R^2$ and $R^3$ are independently
(1) hydrogen,
(2) $C_1$–$C_{10}$ alkyl, or
(3) $C_1$–$C_{10}$ alkyl with 1 to 4 substituents selected from hydroxy, $C_1$–$C_{10}$ alkoxy, and halogen;

x is
(1) —$CH_2$—,
(2) —$CH_2$—$CH_2$—,
(3) —CH=CH—, or
(4) —$CH_2$O—;

$R^4$ and $R^5$ are independently
(1) hydrogen,
(2) $C_1$–$C_{10}$ alkyl,
(3) halogen,
(4) $NHR^8$,
(5) $OR^8$,
(6) $SO_2R^9$, or
(7) $NHSO_2R^9$;

$R^6$ is
(1) hydrogen, or
(2) $C_1$–$C_{10}$ alkyl;

$R^7$ is Z—$(R^{1a})$n;

$R^{1a}$ is
(1) $R^1$, with the proviso that when A is phenyl, $R^{1a}$ is not $C_1$–$C_{10}$ alkyl,
(2) $C_3$–$C_8$ cycloalkyl,
(3) phenyl optionally substituted with up to 4 groups independently selected from $R^8$, $NR^8R^8$, $OR^8$, $SR^8$, and halogen, or
(4) 5- or 6-membered heterocycle with from 1 to 4 heteroatoms selected from oxygen, sulfur, and nitrogen, optionally substituted with up to four groups independently selected from oxo, $R^8$, $NR^8R^8$, $OR^8$, $SR^8$, and halogen;

z is
- (1) phenyl,
- (2) naphthyl,
- (3) a 5- or 6-membered heterocyclic ring with from 1 to 4 heteroatoms selected from oxygen, sulfur, and nitrogen,
- (4) a benzene ring fused to a $C_3$–$C_8$ cycloalkyl ring,
- (5) a benzene ring fused to a 5- or 6-membered heterocyclic ring with from 1 to 4 heteroatoms selected from oxygen, sulfur, and nitrogen,
- (6) a 5- or 6-membered heterocyclic ring with from 1 to 4 heteroatoms selected from oxygen, sulfur, and nitrogen fused to a 5- or 6-membered heterocyclic ring with from 1 to 4 heteroatoms selected from oxygen, sulfur, and nitrogen, or
- (7) a 5- or 6-membered heterocyclic ring with from 1 to 4 heteroatoms selected from oxygen, sulfur, and nitrogen fused to a $C_3$–$C_8$ cycloalkyl ring;

$R^8$ is
- (1) hydrogen,
- (2) $C_1$–$C_{10}$ alkyl,
- (3) $C_3$–$C_8$ cycloalkyl,
- (4) Z optionally having 1 to 4 substituents selected from halogen, nitro, oxo, $NR^{10}OR^{10}$, $C_1$–$C_{10}$ alkyl, $C_1$–$C_{10}$ alkoxy, $C_1$–$C_{10}$ alkylthio, and $C_1$–$C_{10}$ alkyl having 1 to 4 substituents selected from hydroxy, halogen, $CO_2H$, $CO_2$–$C_1$–$C_{10}$ alkyl, $SO_2$—$C_1$–$C_{10}$ alkyl, $C_3$–$C_8$ cycloalkyl, $C_1$–$C_{10}$ alkoxy, and Z optionally substituted by from 1 to 3 of halogen, $C_1$–$C_{10}$ alkyl, or $C_1$–$C_{10}$ alkoxy, or
- (5) $C_1$–$C_{10}$ alkyl having 1 to 4 substituents selected from hydroxy, halogen, $CO_2H$, $CO_2$—$C_1$–$C_{10}$ alkyl, $SO_2$—$C_1$–$C_{10}$ alkyl, $C_3$–$C_8$ cycloalkyl, $C_1$–$C_{10}$ alkoxy, $C_1$–$C_{10}$ alkyl, and Z optionally substituted by from 1 to 4 of halogen, $C_1$–$C_{10}$ alkyl, or $C_1$–$C_{10}$ alkoxy;

$R^9$ is
- (1) $R^8$, or
- (2) $NR^8R^8$;

$R^{10}$ is
- (1) $C_1$–$C_{10}$ alkyl, or
- (2) two $R^{10}$ groups together with the N to which they are attached formed a 5- or 6-membered ring optionally substituted with $C_1$–$C_{10}$ alkyl; or a pharmaceutically acceptable salt thereof.

The present invention also provides novel pharmaceutical formulations of the compounds of Formula I.

The compounds of Formula I are selective $\beta_3$ receptor agonists and as such are useful for treating Type II diabetes and obesity, as well as useful for stimulating the $\beta_3$ receptor. Therefore, the present invention also provides for methods of treating Type II diabetes and obesity, as well as a method of stimulating the $\beta_3$ receptor.

DETAILED DESCRIPTION OF THE INVENTION

For the purposes of the present invention, as disclosed and claimed herein, the following terms, as used herein, are defined below. As they relate to the present invention, the terms below may not be interpreted, individually or collectively, to describe chemical structures that are unstable or impossible to construct.

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atoms fluorine, chlorine, bromine, and iodine.

Examples of 5 and 6-membered heterocycles and fused heterocycles of Z and $R^{1a}$ include pyridyl, quinolinyl, pyrimidinyl, pyrrolyl, thienyl, imidazolyl, thiazolyl, benzimidazolyl, thiadiazolyl, benzothiadiazolyl, indolyl, indolinyl, benzodioxolyl, benzodioxanyl, benzothiophenyl, benzofuranyl, benzoxazinyl, benzisoxazolyl, benzothiazolyl, tetrahydronaphthyl, dihydrobenzofuranyl, tetrahydroquinolinyl, furopyridine and thienopyridine.

The term "fleaving group" as used in the specification is understood by those skilled in the art. Generally, a leaving group is any group or atom that enhances the electrophilicity of the atom to which it is attached for displacement. Preferred leaving groups include but are not intended to be limited to p-nitrobenzene sulfonate, triflate, mesylate, tosylate, imidate, chloride, bromide, iodide, and the like.

The term "pharmaceutically effective amount", as used herein, represents an amount of a compound of the invention that is capable of stimulating the $\beta_3$ receptor in mammals. The particular dose of the compound administered according to this invention will, of course, be determined by the particular circumstances surrounding the patient, including the compound administered, the route of administration, the particular condition being treated, and similar considerations.

The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The term "treating," as used herein, describes the management and care of a patient for the purpose of combating the disease, condition, or disorder and includes the administration of a compound of present invention to prevent the onset of the symptoms or complications, to alleviate the symptoms or complications, or to eliminate the disease, condition, or disorder.

The term "selective" means preferential agonism of the $\beta_3$ receptor over agonism of the $\beta_1$ or $\beta_2$ receptor. In general, the compounds demonstrate a minimum of a twenty fold differential (preferably over a 50× differential) in the dosage required to behave as an agonist to the $\beta_3$ receptor and the dosage required for equal agonism of the $\beta_1$ and $\beta_2$ receptors as measured in the Functional Agonist Assay. The compounds demonstrate this differential across the range of doses. Thus, $\beta_3$ selective compounds behave as agonists for the $\beta_3$ receptor at much lower concentrations with lower toxicity by virtue of their minimal agonism of the other receptors.

As previously noted, the present invention provides a method of treating type II diabetes and obesity, comprising administering to a mammal in need thereof compounds of the Formula I.

The following abbreviations are used throughout the specification:

Boc: tert-butyloxycarbonyl
Cbz: carbobenzyloxy
DIP-Cl: diisopinocampheylchloroborane
DMF: dimethylformamide
DMSO: dimethylsulfoxide
HPLC: high pressure liquid chromatography
Ms: methanesulfonyl (mesyl)
NBS: N-bromosuccinimide
NCS: N-chlorosuccinimide
nHex: n-hexyl
TBAF: tetrabutylammonium fluoride
TBS(TBDMS): t-butyldimethylsilyl
TFA: trifluoroacetic acid
THF: tetrahydrofuran Preferred embodiments of the present invention are set out in paragraphs below.

(a) $X_1$ is —O—$CH_2$.
(b) $R^1$ is hydrogen.
(c) $R^1$ is hydroxy, cyano, oxide, halogen, or trifluoromethyl.
(d) $R^2$ and $R^3$ are independently methyl or hydrogen.
(e) X is —$CH_2$—.
(f) X is —$CH_2$—$CH_2$—.
(g) A is

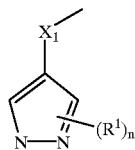

(h) $R^4$ and $R^5$ are independently hydrogen, halogen, $OR^8$, and $NHSO_2R^9$.
(i) $R^4$ and $R^5$ are hydrogen.
(j) Z is phenyl.
(k) Z is naphthyl.
(l) Z is a 5- or 6-membered heterocyclic ring with from 1 to 4 heteroatoms selected from oxygen, sulfur, and nitrogen.

The preferred values of Z are phenyl, naphthyl, benzene ring fused to a 5 or 6-membered heterocyclic ring with from 1 to 4 heteroatoms selected from oxygen, sulfur and nitrogen, or heterocycles with from 1 to 4 heteroatoms independently selected from one of oxygen or sulfur, and/or 1 to 4 nitrogen atoms.

The more preferred values of Z are phenyl, naphthyl, quinolinyl, thienyl, benzimidazolyl, thiadiazolyl, benzothiadiazolyl, indolyl, indolinyl, benzodioxolyl, benzodioxanyl, benzothiophenyl, benzofuranyl, benzoxazinyl, benzisoxazolyl, benzothiazolyl, tetrahydronaphthyl, dihydrobenzofuranyl, triazolyl, tetrazolyl, oxadiazolyl, imidazolyl, oxazolyl, thiazolyl, imidazolidinyl, pyrazolyl, isoxazolyl, pyridyl, pyrimidyl, pyrazolyl, tetrahydrobenzothiazolyl and tetrahydroquinolinyl. When Z is attached to ,$NSO_2(CH_2)_2$-, it is preferably phenyl, naphthyl or a benzene ring fused to a 5 or 6-membered heterocyclic ring with from 1 to 4 heteroatoms selected from oxygen, sulfur and nitrogen, a benzene ring fused to a 5 or 6-membered heterocyclic ring with from 1 to 4 heteroatoms selected from oxygen, sulfur and nitrogen, or a 5 or 6-membered heterocyclic ring with from 1 to 4 heteroatoms selected from oxygen, sulfur and nitrogen fused to a $C_3,C_8$ cycloalkyl ring.

The preferred heterocycles of $R^{1a}$ are thienyl, thiadiazolyl, triazolyl, tetrazolyl, oxadiazolyl, imidazolyl, oxazolyl, thiazolyl, imidazolidinyl, pyrazolyl, isoxazolyl, pyridyl, pyrimidyl, and pyrazolyl.

Certain of the above defined terms may occur more than once in the above formula and upon such occurrence each term shall be defined independently of the other; thus for example, $NR^8R^8$ may represent $NH_2$, $NHCH_3$, $N(CH_3)CH_2CH_3$, and the like.

The compounds of the instant invention all have at least one asymmetric center as noted in structural Formula I. Additional asymmetric centers may be present on the molecule depending upon the nature of the various substituents on the molecule, in particular, $R^2$ and $R^3$. Each such asymmetric center will produce two optical isomers and it is intended that all such optical isomers, as separated, pure or partially purified optical isomers or racemic mixtures thereof, be included within the ambit of the instant invention.

Compounds of the present invention can be prepared according to the Schemes, preparations, and Examples set out below.

Scheme 1

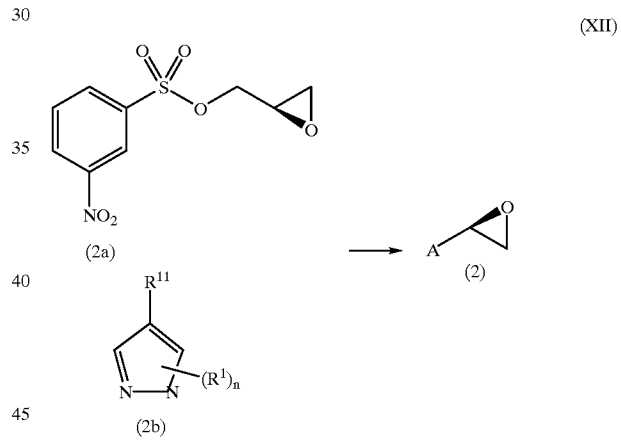

In Scheme 1, $R^{11}$ is OH or SH. Equimolar amounts of the compound (Compound 2b) and (2S)-(+)-glycidyl 3-nitrobenzenesulfonate (Compound 2a) can be dissolved in an inert solvent such as acetone and treated with 1.1 equivalents of a non-reactive acid scavenger, such as $K_2CO_3$. The suspension is then heated at reflux for about 16–20 hours with stirring. The solvent can be removed in vacuo. The residue is partitioned between chloroform or other organic solvent and water. The organic layer can be dried over $Na_2SO_4$ and concentrated in vacuo to give the compound (XI) in sufficient purity (>95%) and yield (85–100%).

Alternatively, the compounds of formula (2), from scheme 1, can be prepared according to Scheme 2. For example, compounds of formula (2b) can be reacted with epichlorohydrin, by methods known in the art, to yield compounds of formula (2c). The compounds of formula (2c) can be closed to the epoxide compounds of formula (2) by methods well known in the art.

Scheme 2

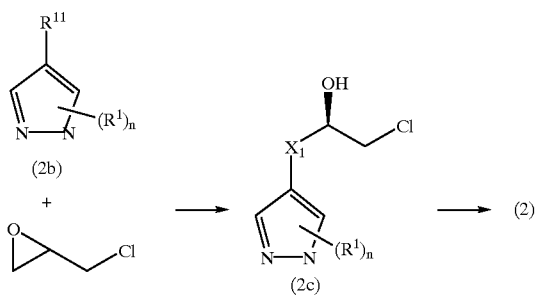

Compounds of formula (3)

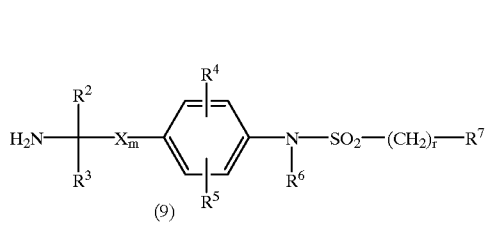

can be conveniently prepared by a variety of methods known to those skilled in the art. A convenient route for the preparation of compounds of formula (3), when $R^6$ is hydrogen, is illustrated in Scheme 3. Compounds of formula (5) are selectively protected as a suitable carbamate derivative (6) with, for example, di-tert-butyl dicarbonate or carbobenzyloxy chloride. These compounds are then treated with a sulfonyl halide, preferably the sulfonyl chloride (7), and a base such as pyridine in an anhydrous solvent such as dichloromethane or chloroform for 0.5 to 24 hours at temperatures of −20° to 50° C., preferably 0° C., to provide the sulfonamides (8). The protecting group is then removed with, for example, trifluoroacetic acid in the case of Boc or catalytic hydrogenation in the case of Cbz, to give the desired amines (9).

Scheme 3

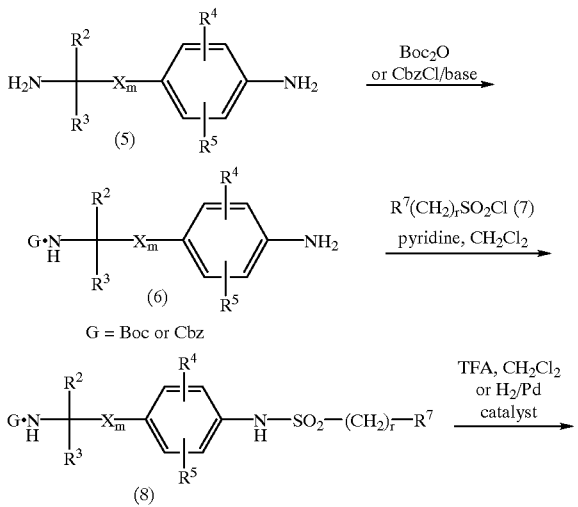

Compounds of formula (3) where $R^6$ is not hydrogen may be conveniently prepared as illustrated in Scheme 4. Sulfonamides (8), prepared as described above, are alkylated with an appropriate alkylating agent (10) in the presence of base to provide sulfonamides (11). Removal of the protecting group as above gives the desired compounds (9a).

Scheme 4

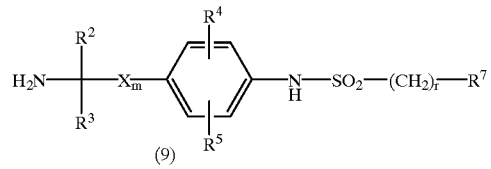

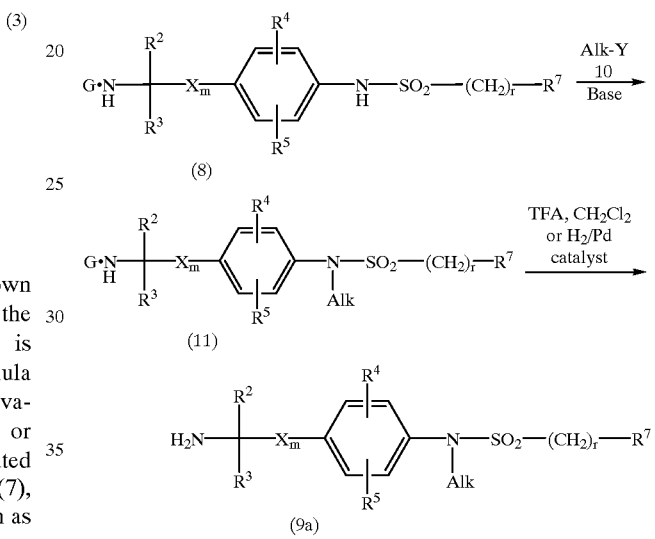

G = Boc or Cbz
Y = Cl, Br, or I
Alk = $C_1$–$C_6$ alkyl

The sulfonyl chlorides (7), many of which are commercially available, can also be readily prepared by a number of methods familiar to those skilled in the art. One suitable method involves the addition of an organolithium reagent or a Grignard reagent to sulfuryl chloride following the procedure of S. N. Bhattacharya, et. al., J Chem. Soc., 1265–1267 (1969). Another convenient method involves the treatment of a thiol with sulfuryl chloride and a metal nitrate according to the procedure of Y. J. Park, et. al., Chemistry Letters, 1483–1486 (1992). Sulfonic acids are also conveniently converted to the corresponding sulfonyl chloride by treatment with PCl, $PCl_3$, or $SOCl_2$, (J. March, Advanced Organic Chemistry, $4^{th}$ Ed., John Wiley and Sons, New York: 1992, p. 1297 and references sited therein). Aromatic and heteroaromatic compounds may be chlorosulfonylated directly by treatment with Vilsmeier's reagent or chorosulfonic acid (Organic Synthesis, I, 8).

The diamines (5) are commercially available or readily prepared by methods described in the literature or known to those skilled in the art. Compounds (5) where $R^2$ or $R^3$ is methyl can be prepared from the corresponding amino acid following the method of J. D. Blooom, et. al., J. Med. Chem., 35, 3081–3084 (1992). As illustrated in Scheme 5 for $R^3$=methyl, the appropriate (R) amino acids (12) are esterified, conveniently by treatment with methanolic hydrochloric acid, and then treated with di-tert-butyl dicarbonate to give compounds (13). The ester group is reduced with a hydride source such as lithium borohydride and the resultant alcohol is converted to a leaving group such as a mesylate. Removal of the Boc protecting groups gives diamines (14). This compound is subjected to catalytic hydrogenation in the presence of base such as sodium acetate to give the desired α-methyl amines (15). The other enantiomer is available through an analogous sequence starting with the corresponding (S) amino acid.

Scheme 5

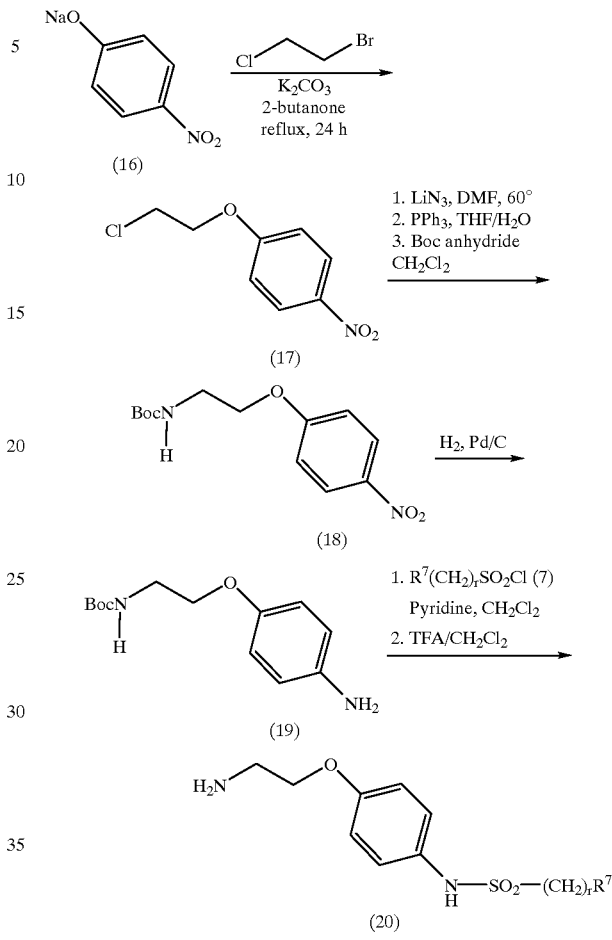

Diamines (5) or sulfonamide amines (9) where X is, CH$_2$O—, and m is 1 are also readily prepared by methods described in the literature or known to those skilled in the art. For example, as shown in Scheme 6, the sodium salt of 4-nitrophenol (16) is alkylated with 1-bromo-2-chloroethane, conveniently in refluxing 2-butanone with a base such as potassium carbonate to give chloro derivative (17). The chloride is converted to the corresponding amine by treatment with lithium azide followed by reduction with, for example, triphenylphosphine in aqueous tetrahydrofuran. Protection of the resultant amine, conveniently as its t-butyl carbamate by treatment with di-tert-butyldicarbonate, gives derivative (18). The nitro group is then reduced, for example, by catalytic hydrogenation to provide amine (19). Acylation of intermediate (19) with sulfonyl chlorides (7), followed by deprotection with acid such as trifluoroacetic acid gives the desired intermediates (20).

Alternatively, diamines (5) where X is ,CH$_2$O— and m is 1 are available from intermediate (19) by treatment with trifluoroacetic acid. This diamine may then be modified as illustrated in Scheme 3.

Diamines (5) and sulfonamide amines (9) where X is CH$_2$CH$_2$— and m is 1 are also readily prepared by methods described in the literature or known to those skilled in the art. For example, as shown in Scheme 7, bromo derivative (21) is treated with sodium cyanide to provide nitrile (22). The nitro group is selectively reduced by treatment with hydrogen and catalytic palladium to provide amine (23). Amine (23) is acylated with sulfonyl chlorides (7) to give the corresponding sulfonamides (24). Reduction of compounds (24) with cobalt chloride and sodium borohydride provides the desired amines (25).

Scheme 7

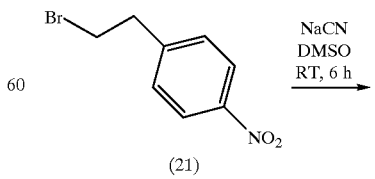

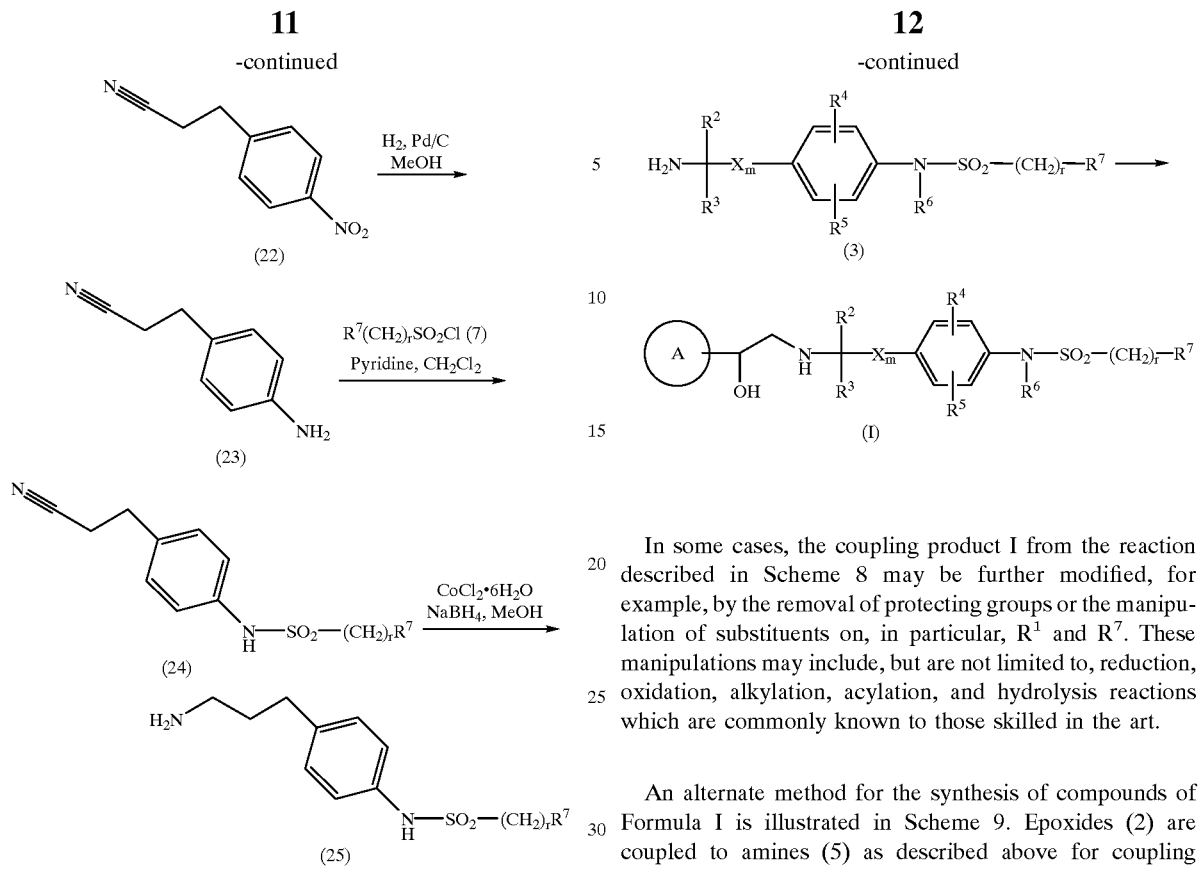

Alternatively, diamines (5) where X is ,CH₂CH₂, and m is 1 are available from intermediates (23) by reduction of the nitrile group with, for example, cobalt chloride and sodium borohydride. This diamine may then be modified as illustrated in Scheme 3.

Referring now to Scheme 8 below, intermediates (2) and (3) are coupled by heating them neat or as a solution in a polar solvent such as methanol, acetonitrile, tetrahydrofuran, dimethylsulfoxide or N-methyl pyrrolidinone for 1 to 24 hours at temperatures of 30° to 150° C. to provide compounds of Formula I as shown in Scheme 8. The reaction is conveniently conducted in refluxing methanol. Alternatively, a salt of amine (3), such as the trifluoroacetate or hydrochloride salt, may be used. In these cases, a base such as sodium bicarbonate or diethylisopropylamine is added to the reaction mixture. The product is purified from unwanted side products by recrystallization, trituration, preparative thin layer chromatography, flash chromatography on silica gel as described by W. C. Still, et. al., J. Org. Chem. 43, 2923 (1978), medium pressure liquid chromatography, or HPLC. Compounds which are purified by HPLC may be isolated as the corresponding salt. Purification of intermediates is achieved in the same manner.

In some cases, the coupling product I from the reaction described in Scheme 8 may be further modified, for example, by the removal of protecting groups or the manipulation of substituents on, in particular, $R^1$ and $R^7$. These manipulations may include, but are not limited to, reduction, oxidation, alkylation, acylation, and hydrolysis reactions which are commonly known to those skilled in the art.

An alternate method for the synthesis of compounds of Formula I is illustrated in Scheme 9. Epoxides (2) are coupled to amines (5) as described above for coupling intermediates (2) and (3) (See Scheme 8) to give aniline derivatives (27). The secondary amines are selectively protected, for example, as a carbamate by treatment with di-tert-butyldicarbonate to provide carbamates (29). Alternatively, nitro amines (26) are used in the coupling reaction to provide (28). Following protection as described above, the nitro group is reduced, for example, by catalytic hydrogenation with palladium catalyst or raney nickel, to provide intermediates (29). In some cases, other groups may be reduced concomitantly. For example, if $R^1$ is halogen in intermediates (28), it may be converted to hydrogen in intermediates (29). Treatment with a sulfonyl chloride in the presence of a base such as pyridine followed by removal of the protecting group with, in the case of a tert-butylcarbamate, acid such as trifluoroacetic acid or methanolic hydrogen chloride, provides the sulfonamides of formula I.

Scheme 8

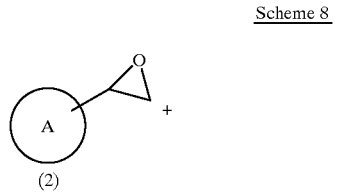

Scheme 9

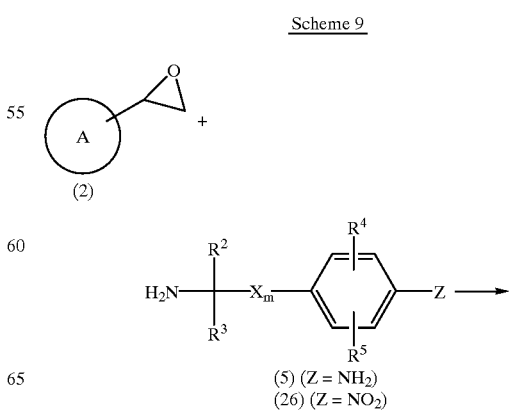

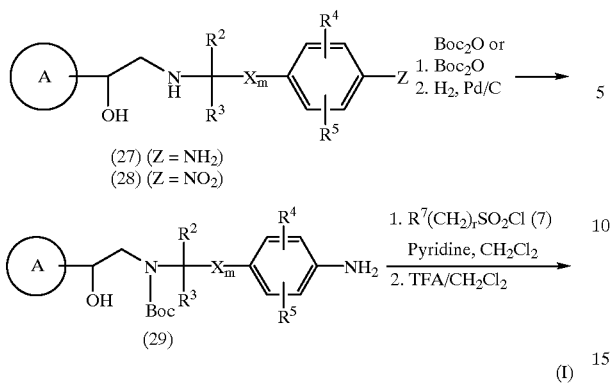

(27) (Z = NH₂)
(28) (Z = NO₂)

In some cases, compounds of formula I from the reaction sequence illustrated in Scheme 9 may be further modified, for example, by the removal of protecting groups or the manipulation of substituents on, in particular, $R^1$ and $R^7$, as described above. In addition, manipulation of substituents on any of the intermediates in the reaction sequence illustrated in Scheme 9 may occur.

The compounds (I) of the present invention can also be prepared from amine intermediates such as those of formula (3) and haloketone intermediates such as those of formula 2d, as shown in Scheme 11. Amines (3) are alkylated with haloketone derivatives (2d), conveniently by treatment of a mixture of (3) and (2d) with base such as potassium carbonate or triethylamine in a polar solvent such as acetonitrile, acetone or dimethylformamide. The resultant aminoketones (32) are reduced with, for example, sodium borohydride in methanol to give the desired compounds of formula (I).

Scheme 11

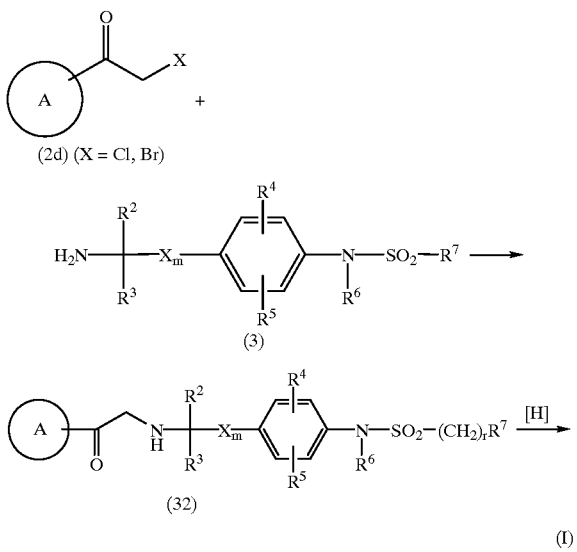

In some cases, the Formula (I) from the reaction described in Scheme 11 may be further modified, for example, by the removal of protecting groups or the manipulation of substituents on, in particular, $R^1$ and $R^7$. These manipulations may include, but are not limited to, reduction, oxidation, alkylation, acylation, and hydrolysis reactions which are commonly known to those skilled in the art.

Scheme 12

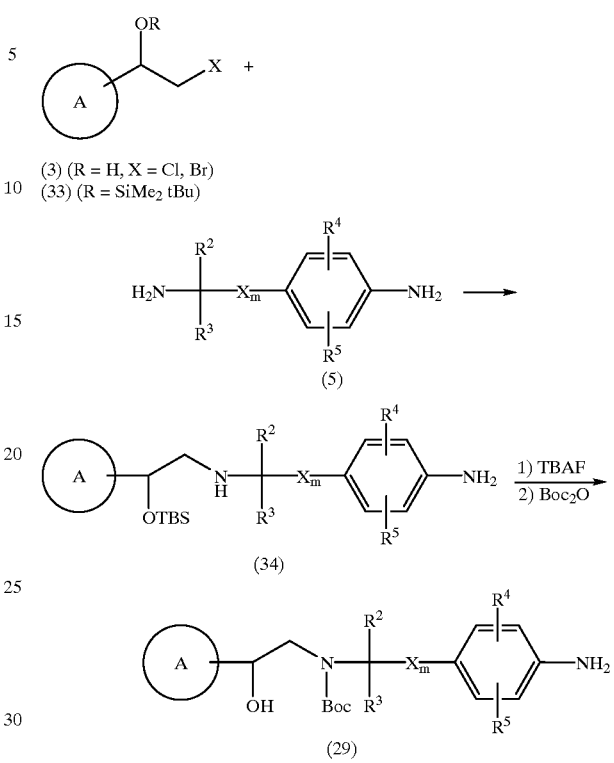

(3) (R = H, X = Cl, Br)
(33) (R = SiMe₂ tBu)

(5)

(34)

(29)

In some cases, compound of formula I may be synthesized directly from intermediates (27) without protection of the secondary amine. For example, when $R^2$ and $R^3$ are both methyl, aniline derivatives (27) are treated with sulfonyl chlorides (7) and a base such as pyridine in a solvent such as dichloromethane at a temperature of −30° to 50° C., typically 0° C., to provide compounds of formula I.

In some cases, the compounds of formula I from the reaction described in Scheme 13 may be further modified, for example, by the removal of protecting groups or the manipulation of substituents on, in particular, $R^1$ and $R^7$, as described above.

Scheme 13

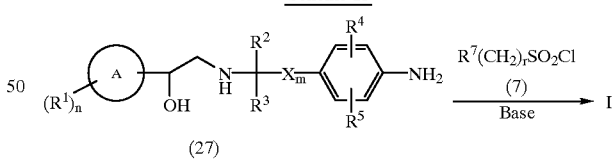

(27)

The compounds (I) of the present invention where $R^2$ and $R^3$ are hydrogen can also be prepared from acid intermediates of formula (36) and aminoalcohols of formula (37), as shown in Scheme 14. Acids (36) are available from the corresponding esters (35), typically a methyl or ethyl ester, by treatment with sulfonyl chlorides (7) and a base such as pyridine, followed by hydrolysis of the ester with aqueous acid or base. Acids (36) are coupled to amines (37), which are known in the literature or readily prepared by methods known to those skilled in the art, using a coupling agent such as benzotriazolyl-N-oxytris(dimethylamino)phosphonium hexafluorophosphate or 1-(3-dimethylaminopropyl)-3-ethylcarbodiimide methiodide to provide the amides (38).

This is treated with a reducing agent, typically borane, to provide the desired compounds of formula I.

Scheme 14

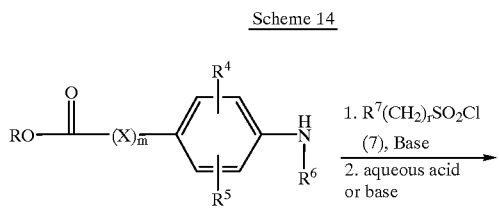

Compounds of the general Formula I may be separated into disastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, an enantiomer of a compound of the general Formula I may be obtained by stereospecific synthesis using optically pure starting materials of known configuration.

PREPARATIONS AND EXAMPLES

The following examples and preparations are provided merely to further illustrate the invention. The scope of the invention is not construed as merely consisting of the following examples. In the following examples and preparations, melting point, nuclear magnetic resonance spectra, mass spectra, N,N-dimethylformamide, palladium on charcoal, tetrahydrofuran, thin layer chromatography and elemental analysis are abbreviated M.Pt., NMR, MS, DMF, Pd/C, THF, EtOAc, TLC. The terms "EA", "NMR", and "MS", when utilized in the preparations, indicate that the data indicated was consistent with the desired structure.

Preparation 1

3,5-Dicarboethoxy-4-Hydroxypyrazole

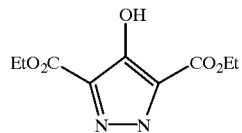

Sodium methoxide (18.9 g, 0.35 moles) was suspended in methanol (400 ml) at 5° C. Dimethylmalonate (46.2, 0.35 moles) and ethyldiazoacetate (20 g, 0.175 moles) was added quickly and the reaction stirred at room temperature for 72 hours. The reaction was cooled to 5° C. and hydrochloric acid (70 ml of 5M) added; followed by 500 ml of water. The pH of the reaction was adjusted to 7 with sodium bicarbonate and the solids (22 g, 63%) collected by filtration. EA, MS Preparation 2

4-Hydroxypyrazole

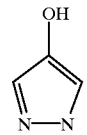

3,5-Dicarboxy-4-hydroxypyrazole (21.5 g, 0.11 moles) was suspended in concentrated hydrochloric acid (200 ml) and heated slowly to reflux. Solids slowly went into solution and gas was evolved. After heating overnight, the solvent was vacuum distilled at 6 mm/Hg up to pot temperature of 80° C. The product (5.02 g, 54%) sublimed out of the pot at 6 mm/Hg and 200° C. EA, MS, NMR Preparation 3

4-t-Butyldimethylsilyloxypyrazole

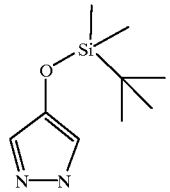

4-Hydroxypyrazole (1.16 g, 13.8 mmol) and imidazole (1.13 g, 16.6 mmol) were suspended in DMF (50 ml) under nitrogen and t-butyldimethylsilylchloride (2.3 g, 15.2 mmol) was added. After stirring 17 hours, the solvent was removed in vacuo and the residue treated with water containing 4.5 g of potassium carbonate. The mixture was extracted with two portions of chloroform and the organic layer dried over sodium sulfate. The solvent was removed in vacuo to yield product (2.58 g, 94%). NMR Preparation 4

1-Benzyl-4-t-Butyldimethylsilyloxypyrazole

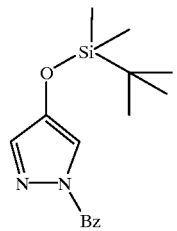

2-t-Butyldimethylsilyloxypyrazole (2.5 g, 12.6 mmol), benzylbromide (2.16 g, 12.6 mmol), and potassium carbonate (3.5m g, 22.5 mmol) was dissolved in DMF (40 ml). The mixture was stirred 17 hours and the solvent removed in vacuo. The residue was taken up in water and extracted with portions of chloroform. The organic layer was washed with brine and dried over sodium sulfate. The solvent was removed and the crude material purified by column chromatography (silica gel, chloroform) to yield product (3.17 g, 61%). EA, MS, NMR Preparation 5

1-Trityl-4-t-Butyldimethylsilyloxypyrazole

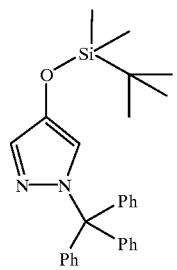

2-t-Butyldimethylsilyloxypyrazole (16.4 g, 0.0827 mol) and trityl chloride were reacted substantially in accordance with preparation 100 to yield product (3.5 g). NMR, MS.

Preparation 6

1-Benzyl-4-Hydroxypyrazole

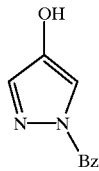

1-Benzyl-4-t-butyldimethylsilyloxypyrazole (3.0 g, 10.4 mmol) was dissolved in THF (20 ml) and tetrabutylammonium fluoride (52 ml of 1M solution in THF) was added. The reaction was stirred overnight and the solvent removed in vacuo. The residue was dissolved in water and extracted into diethylether. The organics dried over sodium sulfate, and the ether removed in vacuo. The residue purified by column chromatography (silica gel, chloroform→2% methanol/chloroform) to yield product (0.63 g, 35%). MS Preparation 7

1-Trityl-4-Hydroxypyrazole

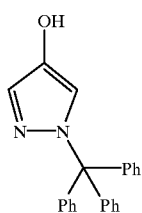

1-Trityl-4-t-butyldimethylsilyloxypyrazole (4.0 g, 9.1 mmol) was reacted substantially in accordance with preparation 102 to yield product (3.5 g). NMR, MS.

Preparation 8

1-Trityl-4-Hydroxypyrazole

4-Hydroxypyrazole (0.5 g, 6 mmol) was dissolved in 50 ml of acetonitrile; triethylamine (3.3 ml, 4 equiv.) and chlorotrimethylsilane (0.9 ml, 1.2 equiv.) was added at room temperature. After two hours of stirring, chlorotriphenylmethane (1.66 g, 1 equiv.) was added and the mixture stirred 16 hours. The mixture was heated to reflux for 30 minutes and the solvent removed in vacuo. The residue was treated with water and sodium bicarbonate powder and then was extracted into ethylacetate, washed with brine, and dried over sodium sulfate. The solvent was once again removed and the residue purified by column chromatography (1:1, hexanes-ethylacetate) to yield product (1.4 g, 73%). NMR, EA, MS. Alternatively the product can be purified by crystallization from methanol instead of through chromatography.

Preparation 9

(s)-1-Benzyl-4-Glycidylpyrazole

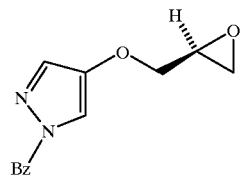

1-Benzyl-4-hydroxypyrazole (2 g, 11.5 mmol), potassium carbonate(3.2 g, 23 mmol), and (2s)-glycidyl-3-nitrobenzenesulfonate (2.98 g, 11.5 mmol) were slurried in actone (300 ml) at reflux for 17 hours. The acetone was removed in vacuo, the residue extracted from brine with chloroform, and dried over sodium sulfate. The solvent was removed again and the residue purified by column chromatography (silica gel, chloroform→1% methanol/chloroform) to yield product (1.8 g, 68%). MS, NMR.

Preparation 10

(s)-1-Trityl-4-Glycidylpyrazole

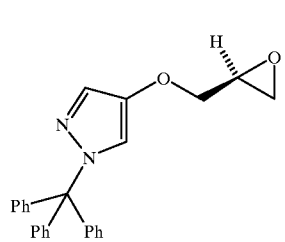

1-Trityl-4-hydroxypyrazole (2.5 g, 7.66 mmol) was reacted substantially in accordance with preparation 105 to yield product (1.75 g). NMR, MS, EA.

Preparation 11

N-(4-[2-Aminoethyl]phenyl)Benzenesulfonamide

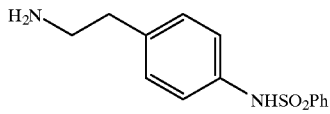

A solution of 4-(2-aminoethyl)aniline hydrochloride salt (10.0 g, 78 mmol) was dissolved in dioxane (200 mL) followed by the addition of 5 M HCl (14.6 ml) and water (25 ml). The solution was cooled in an ice bath and was treated quickly with benzenesulfonyl chloride (10.3 ml, 81 mmol). Pyridine (10 ml) was added and the solution stirred at ambient temperature for 16 h. The solvent was removed under reduced pressure and the residue was dissolved in water (300 ml) and washed with 3 portions of diethylether. The aqueous solution was treated with 80 ml of 5 N sodium hydroxide and was washed again with 3 portions of diethylether. The aqueous phase was adjusted to a pH of approximately 9 by the addition of 40 ml of 5N HCl. The solids were collected and dried. NMR, MS, EA.

Example 1

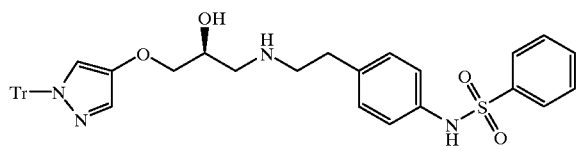

Epoxide from Preparation #10 (382.5 mg, 1 mmol) is dissolved in ethanol (30 ml) and treated with three equivalents of the amine from Preparation #11 (829.1 mg, 3 mmol) and stirred at 80° C. for 16 hours. After cooling to ambient temperature, a white precipitate (excess 368958) appeared and was removed by filtration. The filtrate was concentrated in vacuo and applied to a silica flash chromatography column. Elution with 100% $CHCl_3$ followed by 50:5:1 $CHCl_3/MeOH/NH_4OH$ and concentration of appropriate fractions yielded product as a white solid (535 mg, 81%). NMR, MS, IR.

Example 2

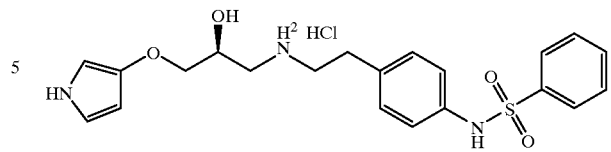

Compound from Example #1 (200 mg, 0.3 mmol) is dissolved in 1N HCl (50 ml) with some THF (5 ml) as a co-solvent and stirred vigorously at ambient temperature for 16 hours. The solution was concentrated in vacuo to yield a hygroscopic white solid (125 mg, 85%). MS, NMR As previously noted, the compounds of the present invention are potent, selective $\beta_3$ receptor agonists. This pharmacological activity can be determined in the functional agonist $\beta_3$ assay.

Functional Agonists

$\beta_3$ Assay

Cell Lines

The $h\beta_2$ DNA was expressed from a plasmid 57537 obtained from American Type Culture Collection. $h\beta_2$ and $h\beta_3$ adrenergic receptors were cloned from human genomic libraries using the polymerase chain reaction method with degenerate probes. Full length receptors were cloned, expressed and sequenced to verify identity according to published sequences ($h\beta_1$:T. Frielle et. al. (1993) *Molecular Pharmacology* 44: 264–270). These receptors were then expressed in the DXB-11 variant of CHO cells using a vector restoring tetrahydrofolate reductase and hygromycin resistance. Rat $\beta_3$ receptor expressing CHO cell line is known in the art. *Mol. Pharm.,* Vol 40, pp. 895–99 (1991). CHO cells were grown in 10% dialyzed FBS./high glucose DMEM/0.1% proline.

cAMP Assay

Cell membranes can be harvested from the above cell line using hypotonic 25 mM Hepes (pH 7.4), 1 mM EDTA, 20 µg/mL leupeptin, 1 mM PMSF buffer with scraping followed by differential centrifugation. Membranes can be incubated in 25 mM Tris (pH 7.6), 0.2% BSA, 2.6 mM Mg, 0.8 mM ATP, 0.1 mM GTP, 5 mM creatine phosphate, creatine kinase 50 U/mL, 0.2 mM IBMX at 32° C. Agonists can be added and incubation continued for 15 m. cAMP produced can be assayed using a fluorescent tracer-immuno assay method.

Intact cell assays can be performed using suspended cells removed from culture flasks by trypsin treatment. Cells can be preincubated with 0.5 mM IBMX at 370C. Agonists can be added and incubation continued for 15 m. Incubation can be stopped by heating suspension in boiling water. cAMP or cGMP in these and the soleus incubations can be assayed by RIA (Amersham).

The compounds of the invention are agonists of the $\beta_3$ receptor. Isoproterenol is accepted in the art as a non-selective $\beta_3$ agonist and is widely used as a comparator in evaluating the activity of compounds. See *Trends in Pharm. Sci.* 15: 3 (1994). In the Functional Agonist $\beta_3$ assay, the compounds would demonstrate at least 30%, preferably 50% and most preferably over 85% of isoproterenol's response at a single dose of 50 mmol. Dose response titrations on the agonists described would reveal $EC_{50}$ values of <10 mM, preferably <1 mmol. In the functional assay, dose titration furnishes an $EC_{50}$ for isoproterenol of 1.1±0.5 mM.

When screened against the $\beta_1$ and $\beta_2$ receptors in the functional assay, dose titration experiments would indicate that greatly reduced or no receptor stimulation is observed with the compounds of the invention. This is defined by measuring the intrinsic activity (maximal response achieved) as compared to isoproterenol. The claimed compounds of Formula I are selective $\beta_3$ receptor agonists and have an intrinsic activity of <3% of isoproterenol's response.

As agonists of $\beta_3$, the compounds are useful in treating conditions in a mammal in which the $\beta_3$ receptor has been demonstrated to have a role in pathology. The preferred mammal is a human. The relationship between modulating the $\beta_3$ receptor and treatment of diseases, such Type II diabetes and obesity, is well established in the art. Other conditions recognized in the art include: gastrointestinal disorders such as gastrointestinal motility, asthma, and depression. Thus, the present compounds are useful in the treatment of inflammatory bowel disease (Crohn's disease or ulcerative colitis), irritable bowel syndrome, non-specific diarrhoea and dumping syndrome.

In treating non-human mammals, the compounds of the present invention are useful for increasing weight gain and/or improving the feed utilization efficiency and/or weight gain and/or improving the feed utilization efficiency and/or increasing lean body mass and/or decreasing birth mortality rate and increasing post/natal survival rate of livestock.

The compounds of Formula I are preferably formulated prior to administration. Therefore, yet another embodiment of the present invention is a pharmaceutical formulation comprising a compound of Formula I and one or more pharmaceutically acceptable carriers, diluents or excipients.

The pharmaceutical formulations of the present invention are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid, or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 0.1 to about 500 mg, more usually about 0.5 to about 200 mg, of the active ingredient. However, it will be understood that the therapeutic dosage administered will be determined by the physician in the light of the relevant circumstances including the condition to be treated, the choice of compound to be administered and the chosen route of administration, and therefore the above dosage ranges are not intended to limit the scope of the invention in any way. The compounds can be administered by a variety of routes including the oral, rectal, transdermal, subcutaneous, topical, intravenous, intramuscular or intranasal routes. For all indications, a typical daily dose will contain from about 0.05 mg/kg to about 20 mg/kg of the active compound of this invention. Preferred daily doses will be about 0.1 to about 10 mg/kg, ideally about 0.1 to about 5 mg/kg. However, for topical administration a typical dosage is about 1 to about 500 mg compound per $cm^2$ of an affected tissue. Preferably, the applied amount of compound will range from about 30 to about 300 $mg/cm^2$, more preferably, from about 50 to about 200 $mg/cm^2$, and, most preferably, from about 60 to about 100 $mg/cm^2$.

The following formulation example is illustrative only and is not intended to limit the scope of the invention in any way.

Formulation 1

Hard gelatin capsules are prepared using the following ingredients:

|  | Quantity (mg/capsule) |
| --- | --- |
| Active Ingredient | 25 |
| starch, dried | 425 |
| magnesium stearate | 10 |
| Total | 460 mg |

The above ingredients are mixed and filled into hard gelatin capsules in 460 mg quantities.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A compound represented by Structural Formula (I):

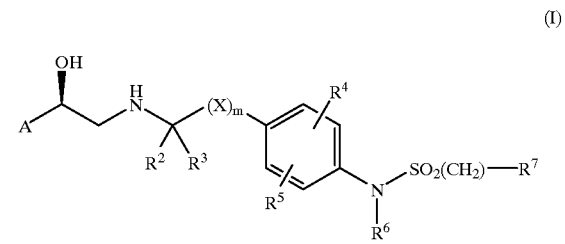

(I)

wherein:

n is 0 or 2;

m is 0 to 5;

A is

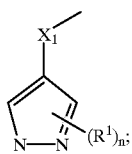

$X_1$ is
  (1) —O—CH$_2$—,
  (2) —S—CH$_2$—, or
  (3) a bond;
$R^1$ is
  (1) hydroxy,
  (2) oxo,
  (3) halogen,
  (4) cyano,
  (5) NR$^8$R$^8$,
  (6) SR$^8$,
  (7) trifluoromethyl,
  (8) C$_1$–C$_{10}$ alkyl,
  (9) OR$^8$,
  (10) SO$_2$R$^9$,
  (11) OCOR$^9$,
  (12) NR$^8$COR$^9$,
  (13) COR$^9$,
  (14) NR$^8$SO$_2$R$^9$,
  (15) NR$^8$CO$_2$R$^8$, or
  (16) C$_1$–C$_{10}$ alkyl substituted by hydroxy, halogen, cyano, NR$^8$R$^8$, SR$^8$, trifluoromethyl, OR$^8$, C$_3$–C$_8$ cycloalkyl, phenyl, NR$^8$COR$^9$, COR$^9$, SO$_2$R$^9$, OCOR$^9$, NR$^8$SO$_2$R$^9$ or NR$^8$CO$_2$R$^8$;
$R^2$ and $R^3$ are independently
  (1) hydrogen,
  (2) C$_1$–C$_{10}$ alkyl, or
  (3) C$_1$–C$_{10}$ alkyl with 1 to 4 substituents selected from hydroxy, C$_1$–C$_{10}$ alkoxy, and halogen;
X is
  (1) —CH$_2$—,
  (2) —CH$_2$—CH$_2$—,
  (3) —CH=CH—, or
  (4) —CH$_2$O—;
$R^4$ and $R^6$ are independently
  (1) hydrogen,
  (2) C$_1$–C$_{10}$ alkyl,
  (3) halogen,
  (4) NHR$^8$,
  (5) OR$^8$,
  (6) SO$_2$R$^9$, or
  (7) NHSO$_2$R$^9$;
$R^6$ is
  (1) hydrogen, or
  (2) C$_1$–C$_{10}$ alkyl;
$R^7$ is Z—(R$^{1a}$)n;
$R^{1a}$ is
  (1) R$^1$,
  (2) C$_3$–C$_8$ cycloalkyl,
  (3) phenyl optionally substituted with up to 4 groups independently selected from R$^8$, NR$^8$R$^8$, OR$^8$, SR$^8$, and halogen, or
  (4) 5- or 6-membered heterocycle with from 1 to 4 heteroatoms selected from oxygen, sulfur, and nitrogen, optionally substituted with up to four groups independently selected from oxo, R$^8$, NR$^8$R$^8$, OR$^8$, SR$^8$, and halogen;

Z is
  (1) phenyl,
  (2) naphthyl,
  (3) a 5- or 6-membered heterocyclic ring with from 1 to 4 heteroatoms selected from oxygen, sulfur, and nitrogen,
  (4) a benzene ring fused to a C$_3$–C$_8$ cycloalkyl ring,
  (5) a benzene ring fused to a 5- or 6-membered heterocyclic ring with from 1 to 4 heteroatoms selected from oxygen, sulfur, and nitrogen,
  (6) a 5- or 6-membered heterocyclic ring with from 1 to 4 heteroatoms selected from oxygen, sulfur, and nitrogen fused to a 5- or 6-membered heterocyclic ring with from 1 to 4 heteroatoms selected from oxygen, sulfur, and nitrogen, or
  (7) a 5- or 6-membered heterocyclic ring with from 1 to 4 heteroatoms selected from oxygen, sulfur, and nitrogen fused to a C$_3$–C$_8$ cycloalkyl ring;
$R^8$ is
  (1) hydrogen,
  (2) C$_1$–C$_{10}$ alkyl,
  (3) C$_3$–C$_8$ cycloalkyl,
  (4) Z optionally having 1 to 4 substituents selected from halogen, nitro, oxo, NR$^{10}$R$^{10}$, C$_1$–C$_{10}$ alkyl, C$_1$–C$_{10}$ alkoxy, C$_1$–C$_{10}$ alkylthio, and C$_1$–C$_{10}$ alkyl having 1 to 4 substituents selected from hydroxy, halogen, CO$_2$H, CO$_2$—C$_1$–C$_{10}$ alkyl, SO$_2$—C$_1$–C$_{10}$ alkyl, C$_3$–C$_8$ cycloalkyl, C$_1$–C$_{10}$ alkoxy, and Z optionally substituted by from 1 to 3 of halogen, C$_1$–C$_{10}$ alkyl, or C$_1$–C$_{10}$ alkoxy, or
  (5) C$_1$–C$_{10}$ alkyl having 1 to 4 substituents selected from hydroxy, halogen, CO$_2$H, CO$_2$—C$_1$–C$_{10}$ alkyl, SO$_2$—C$_1$–C$_{10}$ alkyl, C$_3$–C$_8$ cycloalkyl, C$_1$–C$_{10}$ alkoxy, C$_1$–C$_{10}$ alkyl, and Z optionally substituted by from 1 to 4 of halogen, C$_1$–C$_{10}$ alkyl, or C$_1$–C$_{10}$ alkoxy;
$R^9$ is
  (1) R$^8$, or
  (2) NR$^8$R$^8$;
$R^{10}$ is
  (1) C$_1$–C$_{10}$ alkyl, or
  (2) two R$^1$ groups together with the N to which they are attached formed a 5- or 6-membered ring optionally substituted with C$_1$–C$_{10}$ alkyl; or a pharmaceutically acceptable salt thereof.

2. The compound of claim 1 wherein the compound is represented by the following structural formula:

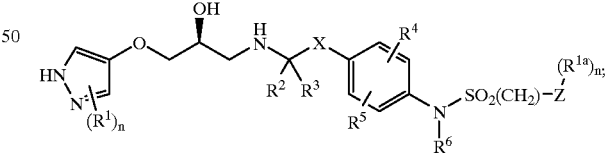

wherein:
$R^2$ and $R^3$ are independently hydrogen or methyl; and
X is methylene or ethylene.

3. The compound of claim 2 wherein Z is phenyl, naphthyl, benzene ring fused to a 5 or 6-membered heterocyclic ring with from 1 to 4 heteroatoms selected from oxygen, sulfur and nitrogen, or heterocycles with from 1 to 4 heteroatoms independently selected from one of oxygen or sulfur, and/or 1 to 4 nitrogen atoms.

4. The compound of claim 3 wherein Z is phenyl, naphthyl, quinolinyl, thienyl, benzimidazolyl, thiadiazolyl, benzothiadiazolyl, indolyl, indolinyl, benzodioxolyl, benzodioxanyl, benzothiophenyl, benzofuranyl, benzoxazinyl, benzisoxazolyl, benzothiazolyl, tetrahydronaphthyl, dihydrobenzofuranyl, triazolyl, tetrazolyl, oxadiazolyl, imidazolyl, oxazolyl, thiazolyl, imidazolidinyl, pyrazolyl, isoxazolyl, pyridyl, pyrimidyl, pyrazolyl, tetrahydrobenzothiazolyl and tetrahydroquinolinyl.

5. The compound of claim 4 wherein:

$R^1$ is hydrogen, hydroxy, cyano, oxide, halogen, or trifluoromethyl; and $R^4$ and $R^5$ are independently hydrogen, halogen, $OR^8$ or $NHSO_2R^9$.

6. The compound of claim 5 wherein Z is phenyl or naphthyl.

7. The compound of claim 6 wherein $R^1$, $R^4$ and $R^5$ are each —H.

8. A method of stimulating beta 3 receptors in a patient in need thereof, said method comprising the step of administering to the patient a pharmaceutically acceptable amount of the compound of claim 1.

9. The method of claim 8 wherein the patient is being treated for obesity or Type II diabetes.

10. The method of claim 9 wherein the compound is represented by the following structural formula:

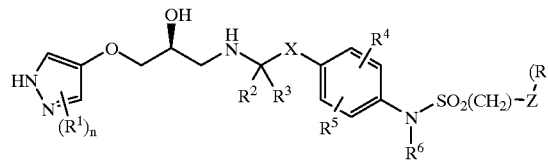

wherein:

$R^2$ and $R^3$ are independently hydrogen or methyl; and

X is methylene or ethylene.

11. The method of claim 10 wherein Z is phenyl, naphthyl, benzene ring fused to a 5 or 6-membered heterocyclic ring with from 1 to 4 heteroatoms selected from oxygen, sulfur and nitrogen, or heterocycles with from 1 to 4 heteroatoms independently selected from one of oxygen or sulfur, and/or 1 to 4 nitrogen atoms.

12. The method of claim 11 wherein Z is phenyl, naphthyl, quinolinyl, thienyl, benzimidazolyl, thiadiazolyl, benzothiadiazolyl, indolyl, indolinyl, benzodioxolyl, benzodioxanyl, benzothiophenyl, benzofuranyl, benzoxazinyl, benzisoxazolyl, benzothiazolyl, tetrahydronaphthyl, dihydrobenzofuranyl, triazolyl, tetrazolyl, oxadiazolyl, imidazolyl, oxazolyl, thiazolyl, imidazolidinyl, pyrazolyl, isoxazolyl, pyridyl, pyrimidyl, pyrazolyl, tetrahydrobenzothiazolyl and tetrahydroquinolinyl.

13. The method of claim 12 wherein:

$R^1$ is hydrogen, hydroxy, cyano, oxide, halogen, or trifluoromethyl; and $R^4$ and $R^5$ are independently hydrogen, halogen, ORB or $NHSO_2R^9$.

14. The method of claim 13 wherein Z is phenyl or naphthyl.

15. The method of claim 14 wherein $R_1$, $R^4$ and $R^5$ are each —H.

16. A pharmaceutical formulation comprising a compound of claim 1 and one or more pharmaceutically acceptable carriers, diluents or excipients.

* * * * *